United States Patent
Fan et al.

(10) Patent No.: US 8,557,784 B2
(45) Date of Patent: Oct. 15, 2013

(54) GLYCYRRHIZINATES OF MORPHINAN DERIVATIVES

(75) Inventors: Chin-Tsai Fan, Tainan (TW); Cheng-Shun Lai, Tainan (TW); Wen-Yen Yeh, Tainan (TW); Yu-Ying Liu, Tainan (TW)

(73) Assignee: Standard Chem. & Pharm. Co., Ltd., Sinying (TW)

( * ) Notice: Subject to any disclaimer, the term of this patent is extended or adjusted under 35 U.S.C. 154(b) by 200 days.

(21) Appl. No.: 13/178,215

(22) Filed: Jul. 7, 2011

(65) Prior Publication Data

US 2013/0012464 A1 Jan. 10, 2013

(51) Int. Cl.
| | |
|---|---|
| *A61K 31/70* | (2006.01) |
| *A61K 31/44* | (2006.01) |
| *C07H 15/24* | (2006.01) |
| *C07H 15/06* | (2006.01) |
| *C13K 5/00* | (2006.01) |
| *C07D 221/22* | (2006.01) |

(52) U.S. Cl.
USPC .............. 514/33; 514/53; 514/289; 536/18.1; 536/18.2; 536/123.13; 546/74

(58) Field of Classification Search
None
See application file for complete search history.

(56) References Cited

PUBLICATIONS

Wan Xu-Ying et. al., "Hepatoprotective and anti-hepatocarcinogenic effects of glycyrrhizin and matrine", *Chemico-Biological Interactions* Sep. 14, 2009;181(1):15-19. Epub May 6, 2009.

Kazuki Abe et. al., "Glycyrrhizin prevents of lipopolysaccharide/D-galactosamine-induced liver injury through down-regulation of matrix metalloproteinase-9 in mice", *J. Pharm. Pharmacol.* Jan. 2008: 60(1):91-97.

M. Tripathi et. al., "Glycyrrhizic acid modulates t-BHP induced apoptosis in primary rat hepatocytes", *Food and Chemical Toxicology* Feb. 2009;47(2009):339-347.

Zhiqian Yu et. al., "Critical roles of platelets in lipopolysaccharide-induced lethality: effects of glycyrrhizin and possible strategy for acute respiratory distress syndrome", *International Immunopharmacology* Mar. 2005: 5(3): 571-580.

Kenjiro Koga et. al., "Novel Formulations of a Liver Protection Drug Glycyrrhizin", Yakugaku Zasshi. Jul. 2007, 127(7):1103-1114.

Takayuki Nagai et. al., "Attenuation of Dysfunction in the Ischemia Reperfused Liver by Glycyrrhizin", *Japan J. Pharmacol.* Mar. 1992; 58(3):209-218.

F. X. Rolaf Van Leeuwen et. al., "The Toxicology of Bromide Ion", *Critical Reviews in Toxicology* 1987;18(3):189-213.

Cem Van Gelderen et. al., "Glycyrrhizin Acid: the Assessment of a No Effect Level", *Human & Experimental Toxicology* Aug. 2000;19(8):434-439.

Wei Zhang et. al., "Neuroprotective effect of dextromethorphan in the MPTP Parkinson's disease model: role of NADPH oxidase", *FASEB J.* Mar. 2004;18(3):589-91. Epub Jan. 20, 2004.

Lyn Patrick, ND, Hepatitis C: Epidemiology and Review of Complementary/Alternative Medicine Treatments, Alternative Medicine Review 1999;4(4):220-238.

Jean-Pierre Daulou Daulouéde et. al., "Preference for buprenorphine/naloxone and buprenorphine among patients receiving buprenorphine maintenance therapy in France: A prospective, multicenter study", *J. Substance Abuse Treatment* Jan. 2010;38(1):83-89.

Kenzie L. Preston. et. al, "Effects of sublingually given naloxone in opioid-dependent human volunteers", *Drug and Alcohol Dependence* 25:27-34, 1990.

*Primary Examiner* — Traviss C McIntosh, III
(74) *Attorney, Agent, or Firm* — Hsiu-Ming Saunders Intellectual Property Connections, Inc.

(57) ABSTRACT

The present invention provides a pharmaceutically acceptable compound, a pharmaceutical composition comprising the above-mentioned pharmaceutically acceptable compound. The pharmaceutically acceptable compound provided by the present invention is a salt of a basic group-containing morphinan derivative and a carboxyl group-containing glycyrrhizinic acid and has the ability to be used to manufacture medicaments for treating and/or preventing cough, ameliorating pains, treating respiratory system diseases, treating cardiovascular diseases and treating liver diseases.

11 Claims, 10 Drawing Sheets

GLYCYRRHIZINATES OF MORPHINAN DERIVATIVES

BACKGROUND OF THE INVENTION

1. Technical Field

The present invention relates to glycyrrhizinates of morphinan derivatives and pharmaceutical use thereof.

2. Description of Related Art

Dextromethorphan and dimemorfan are non-opioid antitussive drugs, safely used in the clinic. 3-Methoxy-morphinan is a dextromethorphan's metabolite. 3-methoxy-morphinan has a spinal anaesthetic effect. 3-methyl-morphinan is a dimemorfan's metabolite. Codeine is an effective narcotic antitussive agent. Buprenorphine is a semi-synthetic narcotic agonist-antagonist analgesic. Butorphanol is a morphinan-type synthetic opioid analgesic. Nalbuphine is a semi-synthetic narcotic agonist-antagonist analgesic. Naloxone is a drug used to counter the effects of opioid overdose. Nalmefene is an opioid receptor antagonist used primarily in the management of alcohol dependence. Naltrexone is an opioid receptor antagonist used primarily in the management of alcohol dependence and opioid dependence. Oxymorphone is a powerful semi-synthetic opioid analgesic.

Dextromethorphan was used as a method of treating chronic pain under U.S. Pat. No. 2,676,177 and for inhibiting the development of tolerance to and/or dependence on a narcotic analgesic under U.S. Pat. No. 5,321,012. The U.S. FDA approved dextromethorphan for over-the-counter sale as a cough suppressant in 1958. The dimemorfan phosphate was discovered through extensive screening of morphinan derivatives and was introduced as an antitussive agent in Japan in 1975. Codeine was used as an opiate for its analgesic, antitussive, and antidiarrheal properties.

Buprenorphine, butorphanol, nalbuphine and oxymorphone are opioids that were indicated for the relief of moderate to severe pain.

Naloxone was used to counter the effects of opioid overdose. Nalmefene was used primarily in the management of alcohol dependence. Naltrexone was used primarily in the management of alcohol dependence and opioid dependence.

Glycyrrhizinic acid has various pharmacological effects. Glycyrrhizinic acid is an ancillary drug used clinically in China for protection of liver function and treatment of tumors (Chem Biol Interact. 2009 Sep. 14; 181(1):15-9. Epub 2009 May 6). Glycyrrhizinic acid has been used as a treatment for chronic hepatitis. Glycyrrhizinic acid reduced the infiltration of inflammatory cells and liver injury (J Pharm Pharmacol. 2008 January; 60(1):91-7). Glycyrrhizinic acid could be beneficial against liver diseases where oxidative stress is known to play a crucial role (Food Chem Toxicol. 2009 February; 47(2):339-47). Glycyrrhizinic acids also have been used for numerous other medical purposes, particularly as an expectorant and a treatment of peptic ulcers. Glycyrrhizinic acid might also be an effective drug against severe acute respiratory syndrome (Int Immunopharmacol. 2005 March; 5(3): 571-80).

Glycyrrhizinic acid has anti-inflammatory activity and has been used for the treatment of chronic viral hepatitis. In Japan, glycyrrhizinic acid injections have been used as a therapeutic drug for allergy inflammation since 1948 and for chronic hepatitis since 1979 (Yakugaku Zasshi. 2007 July; 127(7):1103-14). Glycyrrhizinic acid has been used for the treatment of chronic liver diseases in Japan, and a distinct improvement of liver function tests has been reported (Jpn J. Pharmacol. 1992 March; 58(3):209-18).

Discomfort due to bitter taste is a common complaint from patients, particularly are children and older men, administered some drugs. Dextromethorphan, dimemorfan, codeine, buprenorphine, butorphanol, nalbuphine, naloxone, nalmefene, naltrexone and oxymorphone are morphinan derivatives. Though they very often are used to treat some diseases, but they taste bitter.

Dextromethorphan hydrobromide is a practically odorless, white to almost white crystalline powder with a bitter taste. Dimemorfan phosphate is a white to yellowish-white, odorless, bitter crystals. Codeine base is an odorless crystals or a crystalline powder with a bitter taste.

Opioids usually have a very bitter taste. Buprenorphine is unflavored and has a bitter, medicinal taste (J Subst Abuse Treat. 2010 January; 38(1):83-9). Butorphanol tartrate is a white, crystalline powder that is sparingly soluble in water and insoluble in alcohol. It has a bitter taste. Nalbuphine hydrochloride is an opiate analgesic. It has a bitter taste to patients. Sublingual naloxone has a bitter taste (Drug Alcohol Depend 25:27-34, 1990). Naltrexone hydrochloride occurs as white crystals having a bitter taste.

Due to dextromethorphan is water insoluble, and dextromethorphan must be utilized in the form of a salt, typically the hydrobromide monohydrate salt (dextromethorphan hydrobromide). Dextromethorphan hydrobromide is readily absorbed in the patient's body, but its action is relatively short-lived. The patient is required to take relatively high doses several times a day. It would be very desirable if a form of dextromethorphan that would has more extended-release property is available. Therefore, the dextromethorphan would be slowly released into the patient's bloodstream over a prolonged period of time.

At recommended doses, dextromethorphan hydrobromide produces little or no CNS depression. At higher doses (recreational doses), positive effects may include acute euphoria, elevated mood, dissociation of mind from body, creative dream-like experiences, and increased perceptual awareness. Other effects include disorientation, confusion, pupillary dilation, and altered time perception, visual and auditory hallucinations, and decreased sexual functioning. Abused doses are capable of impairing judgment, memory, language, and other mental performances.

Large doses of bromide cause nausea and vomiting, abdominal pain, coma and paralysis. The chronic state of bromide intoxication is reported as bromism. The signs and symptoms are referable to the nervous system, skin, glandular secretions and gastrointestinal tract (Crit Rev Toxicol. 1987; 18(3):189-213).

Glycyrrhizic (Glycyrrhizinic) acid has relatively mild acute toxicity and glycyrrhizic (glycyrrhizinic) acid is also emphasized by the "generally recognized as safe" (GRAS) status in the USA in 1983 (Hum Exp Toxicol. 2000 August; 19(8):434-9).

SUMMARY OF THE INVENTION

The invention discloses novel compounds comprising dextromethorphan glycyrrhizinate, 3-methoxy-morphinan glycyrrhizinate, dimemorfan glycyrrhizinate, 3-methyl-morphinan glycyrrhizinate, codeine glycyrrhizinate, buprenorphine glycyrrhizinate, butorphanol glycyrrhizinate, nalbuphine glycyrrhizinate, naloxone glycyrrhizinate, nalmefene glycyrrhizinate, naltrexone glycyrrhizinate and oxymorphone glycyrrhizinate, methods for preparing them by reacting dextromethorphan, 3-methoxy-morphinan, dimemorfan, 3-methyl-morphinan, codeine, buprenorphine, butorphanol, nalbuphine, naloxone, nalmefene, naltrexone and oxymorphone with glycyrrhizinic acid. These novel compounds could be used as an antitussive agent, an analgesic agent, a mucolytic agent, a cardiovascular protector and a hepatoprotector for human beings.

In addition, dextromethorphan glycyrrhizinate and dimemorfan glycyrrhizinate are found to be able to increase the e-NOS expression as shown in the Example 3 (which is described below). They could improve endothelial function and attenuate vascular oxidative stress, might be beneficial to cardiovascular diseases, respiratory diseases and liver diseases.

To achieve the object, the present invention provides a pharmaceutically acceptable compound, which is a salt of a basic group-containing agent and a carboxyl group-containing agent and the molar ratio between the basic group-containing agent and the carboxyl group-containing agent ranges from 3:1 to 1:1. The basic group-containing agent is a morphinan derivative, such as dextromethorphan, 3-methoxy-morphinan, dimemorfan, 3-methyl-morphinan, codeine, buprenorphine, butorphanol, nalbuphine, naloxone, nalmefene, naltrexone or oxymorphone. And the carboxyl group-containing agent is glycyrrhizinic acid.

Accordingly, since the pharmaceutically acceptable compound according to the present invention is a new salt prepared by reacting two kinds of active agents, such as (dextromethorphan, glycyrrhizinic acid), (3-methoxy-morphinan, glycyrrhizinic acid), (dimemorfan, glycyrrhizinic acid), (3-methyl-morphinan, glycyrrhizinic acid), (codeine, glycyrrhizinic acid), (buprenorphine, glycyrrhizinic acid), (butorphanol, glycyrrhizinic acid), (nalbuphine, glycyrrhizinic acid), (naloxone, glycyrrhizinic acid), (nalmefene, glycyrrhizinic acid), (naltrexone, glycyrrhizinic acid) or (oxymorphone, glycyrrhizinic acid).

The pharmaceutically acceptable compound according to the present invention is found to be able to exhibit combined pharmacological activities of the morphinan derivatives and glycyrrhizinic acid, so as to achieve a combined therapeutic effects. And the morphinan derivatives are preferable the dextromethorphan, 3-methoxy-morphinan, the dimemorfan, the 3-methyl-morphinan, the codeine, the buprenorphine, the butorphanol, the nalbuphine, the naloxone, the nalmefene, the naltrexone, and the oxymorphone.

With regard to the pharmaceutically acceptable compound of the present invention, since the dextromethorphan, 3-methoxy-morphinan, dimemorfan, 3-methyl-morphinan, codeine, buprenorphine, butorphanol, nalbuphine, naloxone, nalmefene, naltrexone or oxymorphone functions as a base and the glycyrrhizinic acid functions as an acid, the dextromethorphan, 3-methoxy-morphinan, dimemorfan, 3-methyl-morphinan, codeine, buprenorphine, butorphanol, nalbuphine, naloxone, nalmefene, naltrexone or oxymorphone and the glycyrrhizinic acid can react with each other to form salts.

The glycyrrhizinic acid, as shown in Formula I as below, contains three carboxyl group (labeled with numerals 1, 2, and 3) to act with the morphinan derivatives base to form the salts through any one, any two, or even all of the three carboxyl groups. Therefore, in the resultant salt, the molar ratio between the morphinan derivatives and the glycyrrhizinic acid ranges from 3:1 to 1:1, and is preferable of 1:1.

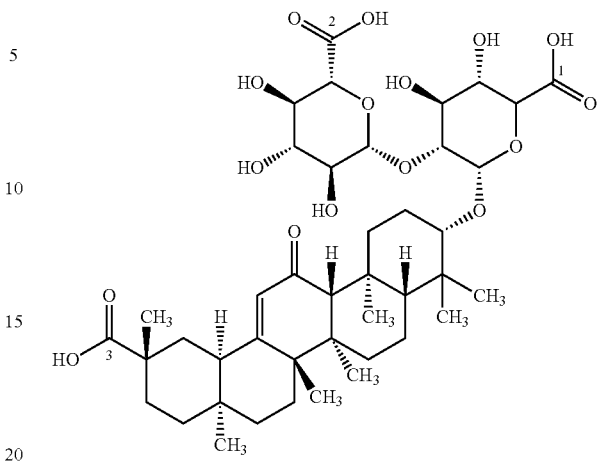

Formula I

The pharmaceutically acceptable compound according to the present invention has unique characteristics distinguishable from either dextromethorphan, 3-methoxy-morphinan, dimemorfan, 3-methyl-morphinan, codeine, buprenorphine, butorphanol, nalbuphine, naloxone, nalmefene, naltrexone or oxymorphone alone or glycyrrhizinic acid alone, based on the testing results in IR, MS and NMR analyses.

Until the present invention described herein, there is not any report about a dextromethorphan glycyrrhizinate compound, a 3-methoxy-morphinan glycyrrhizinate compound, a dimemorfan glycyrrhizinate compound, a 3-methyl-morphinan glycyrrhizinate compound, a codeine glycyrrhizinate compound, a buprenorphine glycyrrhizinate compound, a butorphanol glycyrrhizinate compound, a nalbuphine glycyrrhizinate compound, a naloxone glycyrrhizinate compound, a nalmefene glycyrrhizinate compound, a naltrexone glycyrrhizinate compound or an oxymorphone glycyrrhizinate compound.

These compounds described above might be able to achieve combined pharmacological activities. Salt formation provides an action of altering the physicochemical and resultant biological characteristics of a drug without modifying its chemical structure. A salt form can have a dramatic influence on the properties of the drug.

Dextromethorphan can reduce the inflammation reactions. Dextromethorphan can improve endothelial function and attenuate vascular oxidative stress and inflammation. Dextromethorphan could significantly reduce the production of both extracellular superoxide free radicals and intracellular reactive oxygen species (ROS) (FASEB J. 2004 March; 18(3):589-91. Epub 2004 Jan. 20). Therefore, dextromethorphan might reduce systemic inflammatory responses to provide the protective effect in liver. The dextromethorphan glycyrrhizinate could have the combined liver protection pharmacology effects and therapeutic effects of glycyrrhizinic acid and dextromethorphan.

Dimemorfan could decrease production of reactive oxygen species (ROS) and expression in neutrophils. Dimemorfan could also inhibit LPS-induced ROS and nitric oxide (NO) production. Therefore, dimemorfan might reduce systemic inflammatory responses to provide the protective effect in liver. The dimemorfan glycyrrhizinate could have the combined liver protection pharmacology effects and therapeutic effects of glycyrrhizinic acid and dimemorfan. Naltrexone or nalmefene could be used as a pharmaceutical composition for treating liver damage, treating infections caused by hepatitis B or C virus under U.S. Pat. No. 7,501,433.

It has now been found that the morphinan derivatives, dextromethorphan glycyrrhizinate, 3-methoxy-morphinan glycyrrhizinate, dimemorfan glycyrrhizinate, 3-methyl-morphinan glycyrrhizinate, codeine glycyrrhizinate, buprenorphine glycyrrhizinate, butorphanol glycyrrhizinate, nalbuphine glycyrrhizinate, naloxone glycyrrhizinate, nalmefene glycyrrhizinate, naltrexone glycyrrhizinate and oxymorphone glycyrrhizinate compounds, may be converted into the compositions, dextromethorphan and glycyrrhizinic acid, 3-methoxy-morphinan and glycyrrhizinic acid, dimemorfan and glycyrrhizinic acid, 3-methyl-morphinan and glycyrrhizinic acid, codeine and glycyrrhizinic acid, buprenorphine and glycyrrhizinic acid, butorphanol and glycyrrhizinic acid, nalbuphine and glycyrrhizinic acid, naloxone and glycyrrhizinic acid, nalmefene and glycyrrhizinic acid, naltrexone and glycyrrhizinic acid, oxymorphone and glycyrrhizinic acid in the body after administering to human. These morphinan derivatives can have antitussive activity, analgesic activity, mucoregulatory activity, cardiovascular protection activity or liver protection activity and may be used as an antitussive agent, an analgesic agent, a mucolytic agent, a cardiovascular protector and a hepatoprotector.

The novel salt of the present invention has properties which are particularly suitable for use as a drug, including improving the taste, altering the solubility or absorption and increasing the related therapeutic effects. Dextromethorphan, dimemorfan, codeine, buprenorphine, butorphanol, nalbuphine, naloxone, nalmefene, naltrexone and oxymorphone are morphinan derivatives, they all taste bitter. Glycyrrhizinic acid is a sweetener and odorant. Though glycyrrhizin still has the some disadvantages as its additional astringent and medicinal tastes, the sweetness of the substance is much more delayed than that of sucrose. However, it has now been surprisingly found that the dextromethorphan glycyrrhizinate, dimemorfan glycyrrhizinate, codeine glycyrrhizinate, buprenorphine glycyrrhizinate, butorphanol glycyrrhizinate, nalbuphine glycyrrhizinate, naloxone glycyrrhizinate, nalmefene glycyrrhizinate, naltrexone glycyrrhizinate and oxymorphone glycyrrhizinate compounds have the ability to improve the bitter-tasting flavor and could be accepted by patients, particularly such as children and the elderly.

Orally disintegrating tablet (ODT) has made taking medication easier, especially for children and the elderly. The single most significant issue with ODT is the bitterness of the drug. Skillful taste masking is needed to hide this bitterness. The dextromethorphan glycyrrhizinate, dimemorfan glycyrrhizinate, codeine glycyrrhizinate, buprenorphine glycyrrhizinate, butorphanol glycyrrhizinate, nalbuphine glycyrrhizinate, naloxone glycyrrhizinate, nalmefene glycyrrhizinate, naltrexone glycyrrhizinate and oxymorphone glycyrrhizinate compounds would might be some skillful taste masking agents.

Sublingual tablet is a dosage form that dissolves when held beneath the tongue, permitting direct absorption of the active ingredient by the oral mucosa. Buccal tablet is a dosage form that dissolves when held between the cheek and gum, permitting direct absorption of the active ingredient through the oral mucosa. Solution or syrup is a dosage form that is convenient for children, the elderly and the dysphagia people. The most significant issue with sublingual tablet, buccal tablet, solution or syrup is the bitterness of the drug. The morphinan derivatives are bitter drugs originally. According to this novel invention, the morphinan derivatives will transfer into the morphinan derivatives glycyrrhizinates, which are sweet drugs, they will be more suitable to sublingual tablet, buccal tablet, solution or syrup and they will be more easily accepted by patients.

Furthermore, as discussed previously, dextromethorphan base is water insoluble, and dextromethorphan must be utilized in the form of a salt. Therefore, dextromethorphan glycyrrhizinate could improve dextromethorphan base's solubility and absorption.

Hydrobromide is a stronger acid. Glycyrrhizinic acid is a weak acid. The three dissociation constants of glycyrrhizinic acid are about 3.98 (pKa1), 4.62 (pKa2) and 5.17 (pKa3), respectively. Hydrobromide (HBr) is a strong acid. Hydrobromide (HBr)'s pKa is about −9. pKa is equal to −log Ka, the Ka (Acidity constant) is equal to $[H^+][A^-]/[HA]$. Hydrochloride (HCl)'s pKa is about −7, HBr is a stronger acid than HCl. Therefore, a glycyrrhizinic acid would be possible to conjugate more tightly to dextromethorphan than a hydrobromide does. As shown in the Example 4 (which is described below), the solubility of dextromethorphan glycyrrhizinate is less than dextromethorphan hydrobromide. Dextromethorphan glycyrrhizinate might have more extended-release property than dextromethorphan hydrobromide.

As discussed previously, acute effects of bromide may include CNS depression, coma, hypotension, tachycardia, and respiratory distress. Ingestion of chronic bromide, excessive amounts may produce a toxic syndrome, "bromism". Chronic intoxication usually develops over 2 to 4 weeks or longer. For the phosphate, the most frequently seen effect following ingestion phosphate or rectal phosphate administration is gastrointestinal irritation. If a significant amount of phosphate is absorbed, hyperphosphatemia, hypocalcemia, and hypomagnesemia may occur. For the glycyrrhizinic acid, glycyrrhizinic acid has relatively mild acute toxicity, and glycyrrhizinic acid is also emphasized by the "generally recognized as safe" (GRAS) status in the USA in 1983.

The present invention overcomes limitations in the prior art by providing a dextromethorphan glycyrrhizinate that essentially or completely eliminates the risk of bromide toxicity. The glycyrrhizin salt of dextromethorphan, besides being new, more especially, overcomes the previously mentioned deficiencies of the hydrobromide salt of dextromethorphan.

Dimemorfan phosphate might have the side effects, such as change in glucose tolerance, dizziness, drowsiness, dry mouth, nausea, vomiting, malaise, tachycardia, palpitations and hot flushes.

For the phosphate, the most frequently seen effect following ingestion phosphate or rectal phosphate administration is gastrointestinal irritation. If a significant amount of phosphate is absorbed, hyperphosphatemia, hypocalcemia, and hypomagnesemia may occur.

The present invention overcomes limitations in the prior art by providing a dimemorfan glycyrrhizinate that essentially or completely eliminates the side effect of phosphate. The glycyrrhizin salt of dimemorfan, besides being new, more especially, overcomes the previously mentioned deficiencies of the phosphate salt of dimemorfan.

It has now been found that it is possible to provide a base of dextromethorphan or dimemorfan by reacting it with glycyrrhizinic acid so as to form dextromethorphan glycyrrhizinate or dimemorfan glycyrrhizinate. The dextromethorphan glycyrrhizinate or dimemorfan glycyrrhizinate might have more safe property than dextromethorphan hydrobromide or dimemorfan phosphate. Therefore, the pharmaceutically acceptable compound provided by the present invention, such as the dextromethorphan glycyrrhizinate, essentially or completely eliminates the risk of bromide toxicity.

Dextromethorphan hydrobromide is readily absorbed in the patient's body, but its action is relatively short-lived. The patients require to take relatively high doses several times a day. It has now been found that dextromethorphan glycyrrhizinate could improve dextromethorphan base's solubility and absorption, could have more extended-release property than dextromethorphan hydrobromide and have longer action duration in the patient's body.

In the field of pharmaceutics, glycyrrhizinic acid is used to enhance the transdermal absorption of drugs. Glycyrrhizinic acid has been reported to possess in vivo enhancing activity with respect to the nasal and rectal absorptions of antibiotics, insulin, and calcitonin.

Nalbuphine has been reported to have a short half-life and bioavailability. However, it is found that nalbuphine glycyrrhizinate and nalbuphine have various physicochemical properties. Nalbuphine glycyrrhizinate may be converted into the nalbuphine and glycyrrhizinic acid, in the body after administration. Glycyrrhizinic acid can enhance the absorption of nalbuphine. Therefore, nalbuphine glycyrrhizinate could have more bioavailability.

In Japan, glycyrrhizinic acid has been an accepted treatment of chronic hepatitis for over 20 years. Both glycyrrhizinic acid and glycyrrhetinic acid have been found to possess antiviral activity. Glycyrrhizinic acid significantly decreased lipid peroxides and transaminase levels, both oral and intravenous routes of administration glycyrrhizinic acid appear to have hepatoprotective properties (Altern Med Rev 1999; 4(4):220-238). Glycyrrhizinic acid also appears to work as a free radical scavenger.

Dextromethorphan glycyrrhizinate and dimemorfan glycyrrhizinate have the ability to increase the e-NOS expression as shown in the Example 3. They could improve endothelial function and attenuate vascular oxidative stress, and therefore might reduce systemic inflammatory responses to provide the protective effect in liver and cardiovascular and respiratory system.

Accordingly, the pharmaceutically acceptable compound provided by the present invention, such as the dextromethorphan glycyrrhizinate, 3-methoxy-morphinan glycyrrhizinate, dimemorfan glycyrrhizinate, 3-methyl-morphinan glycyrrhizinate, codeine glycyrrhizinate, buprenorphine glycyrrhizinate, butorphanol glycyrrhizinate, nalbuphine glycyrrhizinate, naloxone glycyrrhizinate, nalmefene glycyrrhizinate, naltrexone glycyrrhizinate and oxymorphone glycyrrhizinate, has the combined pharmacology activities in antitussive activity, analgesic activity, mucoregulator activity, cardiovascular protection activity and/or liver protection activity, and might offer combined therapeutic effects.

These pharmaceutically acceptable compounds provided by the present invention, such as dextromethorphan glycyrrhizinate, 3-methoxy-morphinan glycyrrhizinate, dimemorfan glycyrrhizinate, 3-methyl-morphinan glycyrrhizinate, codeine glycyrrhizinate, buprenorphine glycyrrhizinate, butorphanol glycyrrhizinate, nalbuphine glycyrrhizinate, naloxone glycyrrhizinate, nalmefene glycyrrhizinate, naltrexone glycyrrhizinate or oxymorphone glycyrrhizinate has the ability to be used to manufacture medicaments for treating and/or preventing cough, ameliorating pains, treating respiratory system diseases, treating cardiovascular diseases and treating liver diseases.

The present invention also provides a pharmaceutical composition that comprises an active ingredient that is the above-mentioned pharmaceutically acceptable compound and a pharmaceutically acceptable carrier, diluent or excipient. Therefore, the pharmaceutical composition comprising the pharmaceutically acceptable compound provided by the present invention is suitable for use in transnasal, transdermal, rectal, oral treatment or parenteral injection. In other words, the pharmaceutically acceptable compounds may be liquid or solid for topical, buccal, oral or parenteral administration in form of tablets, capsules and pills eventually with enteric coating, powders, granules, pellets, emulsions solutions, suspensions, syrups, elixir, ointments, creams, injectable forms or liposomes.

The present invention further provides a method for preparing the above-mentioned pharmaceutically acceptable compound, comprising the following steps: (1) dissolving the basic group-containing morphinan derivative, such as dextromethorphan, 3-methoxy-morphinan, dimemorfan, 3-methoxy-morphinan, codeine, buprenorphine, butorphanol, nalbuphine, naloxone, nalmefene, naltrexone and oxymorphone, in a free base form or in a salt form and the carboxyl group-containing glycyrrhizinic acid in a free acid form or in a salt form in a first solvent to form a solution; and (2) removing the first solvent from the solution or mixing the solution with a second solvent to obtain the pharmaceutically acceptable compound.

Also within the scope of this invention is a method for treating cough, all sort of pains, respiratory system diseases, cardiovascular diseases and liver diseases by administering to a subject in need thereof an effective amount of the above-mentioned pharmaceutically acceptable compounds.

DETAILED DESCRIPTION OF THE PREFERRED EMBODIMENT

Figure 1:
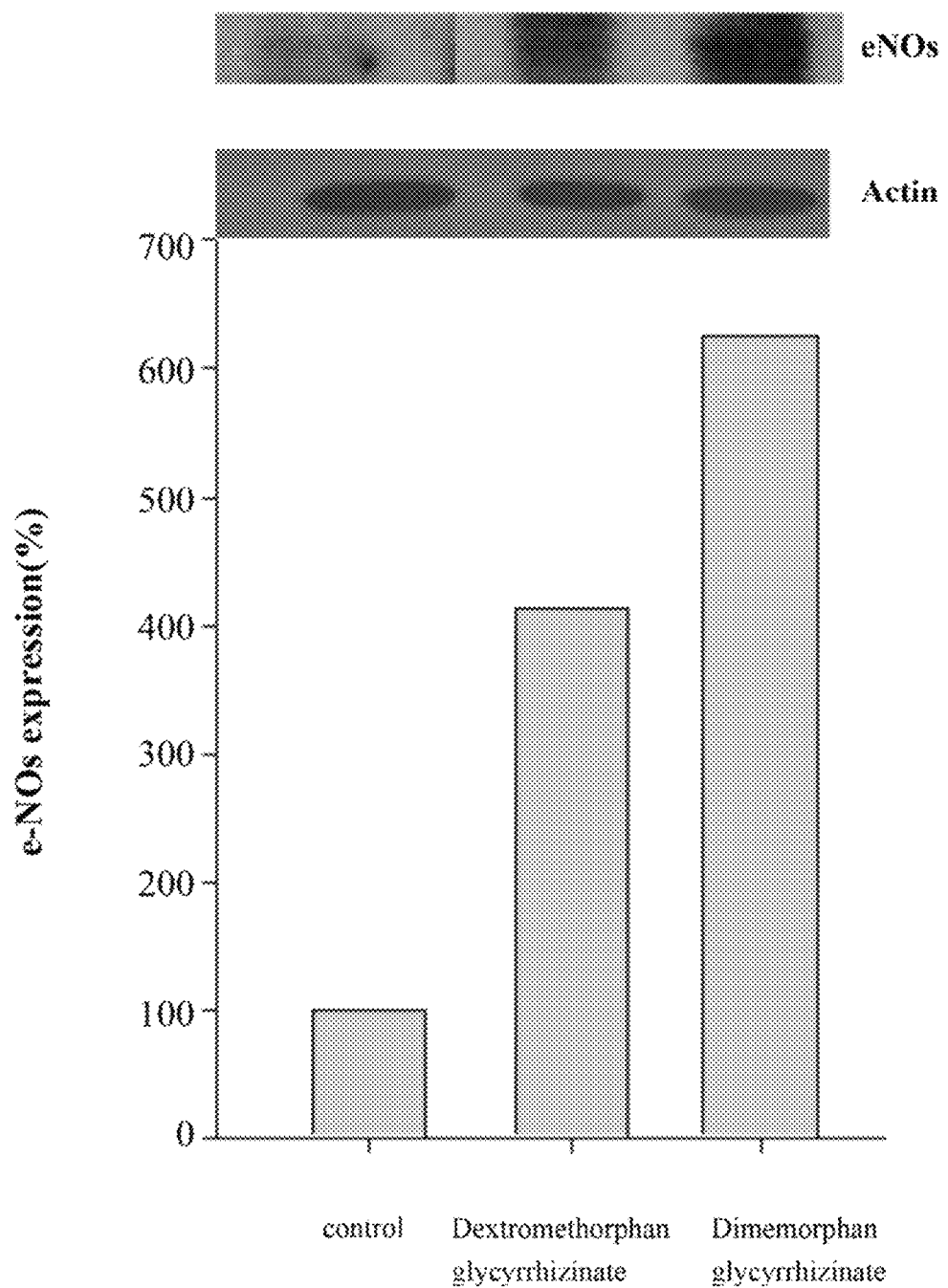
FIG. 1 shows a diagram of e-NOS expression of dextromethorphan glycyrrhizinate and dimemorfan glycyrrhizinate.

The present invention discloses a pharmaceutically acceptable compound that is a salt of a basic group-containing morphinan derivative and a carboxyl group-containing glycyrrhizinic acid.

Preparation of the Glycyrrhizinates of Morphinan Derivatives

According to the present invention, the pharmaceutically acceptable compounds provided by the present invention are preferably formed by the interaction of the carboxyl group-containing glycyrrhizinic acid with the basic group-containing morphinan derivative, such as dextromethorphan, 3-methoxy-morphinan, dimemorfan, 3-methoxy-morphinan, codeine, buprenorphine, butorphanol, nalbuphine, naloxone, nalmefene, naltrexone or oxymorphone.

The pharmaceutically acceptable compounds may be readily filtered and easily dried, and, if necessary, can be easily re-purified by re-dissolving the compound in a suitable solvent followed by drying to remove the solvent. The resulting solution can also be mixed with another suitable solvent to precipitate the pharmaceutically acceptable compound.

For example, the pharmaceutically acceptable compounds may be prepared in accordance with the following process:

To a round bottom flask equipped with a magnetic stirrer are charged a basic group-containing morphinan derivative in a free base form or in a salt form, the carboxyl group-containing glycyrrhizinic acid in a free acid form or in a salt form, and a first solvent.

The basic group-containing morphinan derivative is preferable, but not limited to, dextromethorphan, 3-methoxy-morphinan, dimemorfan, 3-methoxy-morphinan, codeine, buprenorphine, butorphanol, nalbuphine, naloxone, nalmefene, naltrexone or oxymorphone compound.

The resulting reaction mixture is allowed to agitate at a certain temperature for a certain period of time until it is dissolved completely. The resulting solution is concentrated via reduced pressure distillation and the desired dextromethorphan glycyrrhizinate compound, 3-methoxy-morphinan glycyrrhizinate compound, dimemorfan glycyrrhizinate compound, 3-methoxy-morphinan glycyrrhizinate compound, codeine glycyrrhizinate compound, buprenorphine glycyrrhizinate compound, butorphanol glycyrrhizinate compound, nalbuphine glycyrrhizinate compound, naloxone glycyrrhizinate compound, nalmefene glycyrrhizinate compound, naltrexone glycyrrhizinate compound or oxymorphone glycyrrhizinate compound is thus obtained.

The first solvent used might be any solvent in which the basic group-containing morphinan derivative and the carboxyl group-containing glycyrrhizinic acid can be well dissolved, and preferably to be water, $C_{1-8}$ straight or branched alcohols, acetone, methyl ethyl ketone, methyl isobutyl ketone, dichloromethane, diethyl ether, diisopropyl ether, dimethyl sulfoxide, N,N'-dimethylformamide, N,N'-dimethylacetamide, and a mixture of the above-mentioned solvents thereof.

In addition, any other conventional methods, besides reduced pressure distillation, to remove the first solvent can be used in the present invention. The preferred methods for removing the first solvent include, but are not limited to, concentrated and crystallized by natural evaporation, vacuum concentration, or drying under nitrogen.

The resulting solution can be also mixed with a second solvent to precipitate the above-mentioned pharmaceutically acceptable compound. The second solvent used might be any solvent, which is miscible with the first solvent and can cause the precipitation of the pharmaceutically acceptable compound, such as acetonitrile, ethanol, acetone, methyl ethyl ketone, dichloromethane, diethyl ether, diisopropyl ether, or the combination thereof.

The present invention also provides a pharmaceutical composition that comprises an active ingredient that is the above-mentioned pharmaceutically acceptable compound and a pharmaceutically acceptable carrier, diluent or excipient.

The present invention further provide a method for preparing the above-mentioned pharmaceutically acceptable compound, comprising the following steps:
(1) dissolving the basic group-containing morphinan derivatives in a free base form or in a salt form and the carboxyl group-containing glycyrrhizinic acid in a free acid form or in a salt form in a first solvent to form a solution; and
(2) removing the first solvent from the solution or mixing the solution with a second solvent to obtain the pharmaceutically acceptable compound.

The present invention also provides a method for offering a therapeutic effect, such as treating cough, ameliorating pains, treating respiratory system disease, treating cardiovascular disease and treating liver disease. The method comprises the step of administering to a subject in need thereof an effective amount of the above-mentioned pharmaceutically acceptable compound.

Several specific examples of this invention are described in details and as below, and are provided only for purpose of illustration and are not intended to limit the scope of the invention as disclosed in the claims.

Example 1

Preparation of Dextromethorphan Glycyrrhizinate Compound by Dextromethorphan Free Base and Glycyrrhizinic Acid Dextromethorphan free base (0.495 g, 1.82 mmol) and glycyrrhizinic acid (1.500 g, 1.82 mmol) were thoroughly mixed and then added to 24 ml isopropyl alcohol. The resultant mixture was then heated at reflux to provide a clear solution. The resulting clear solution was cooled at 25~30° C., and stirred for 1 hour. The precipitated solid was filtered and washed with 20 ml acetone and dried to produce 1.4 g of dextromethorphan glycyrrhizinate.

FT-IR, MS and NMR analyses of dextromethorphan glycyrrhizinate are carried out for determining the physical and chemical characteristics of the resultant dextromethorphan glycyrrhizinate. And dextromethorphan and glycyrrhizinic acid are also tested at the same time for a blank control.

Figure 2:
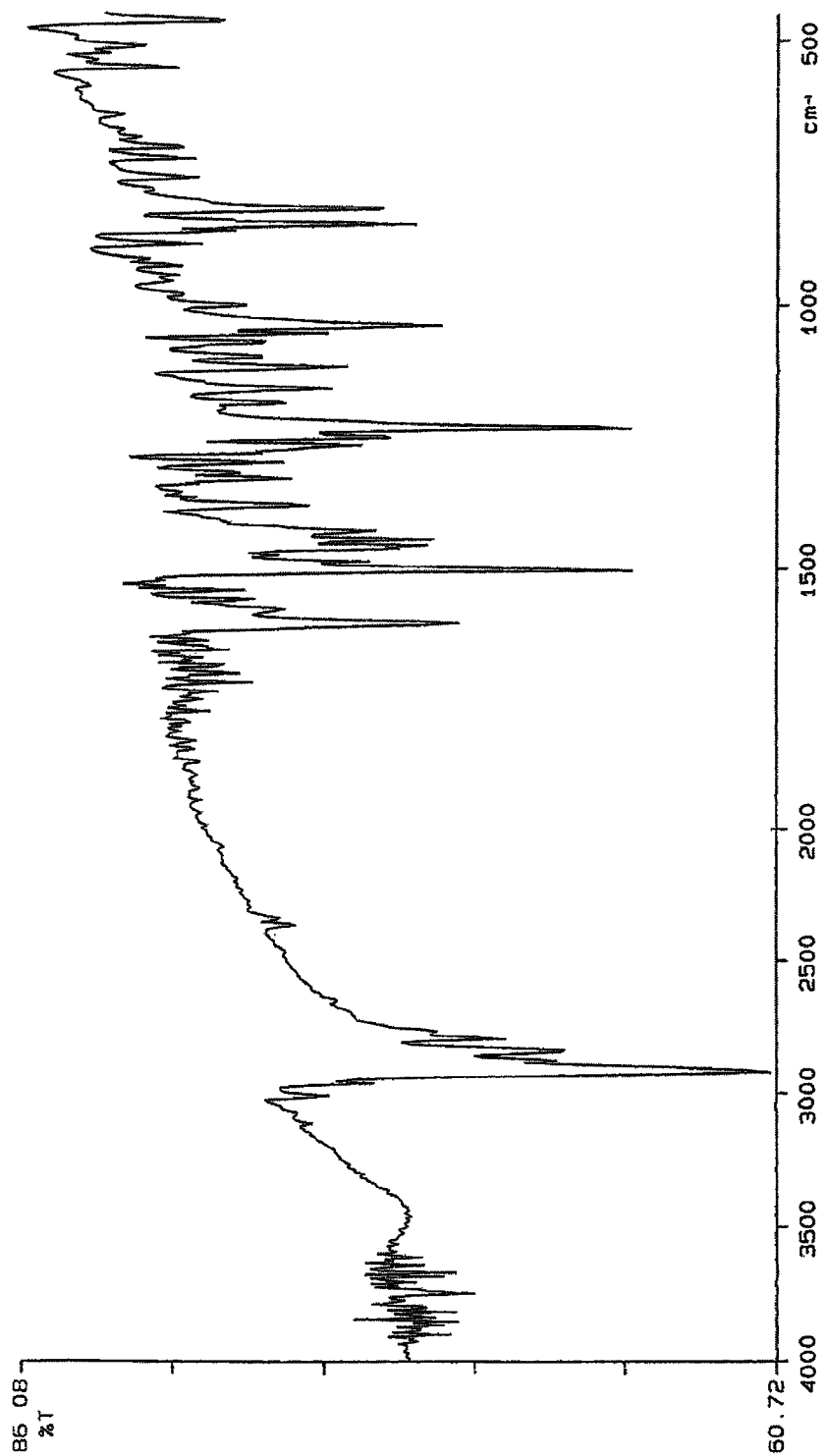
FIG. 2 is an infrared spectrum of dextromethorphan.
Figure 3:
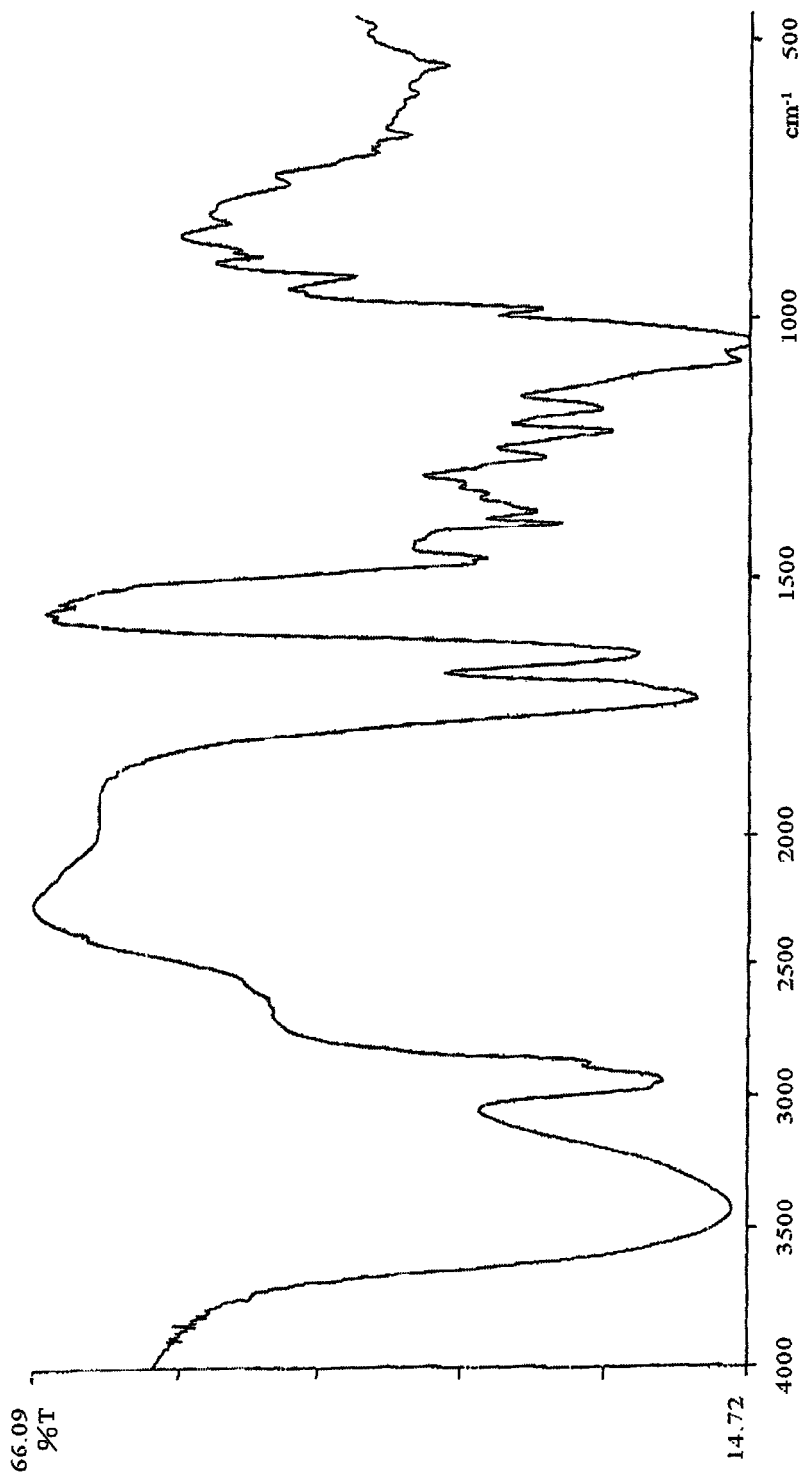
FIG. 3 is an infrared spectrum of glycyrrhizinic acid.
Figure 4:
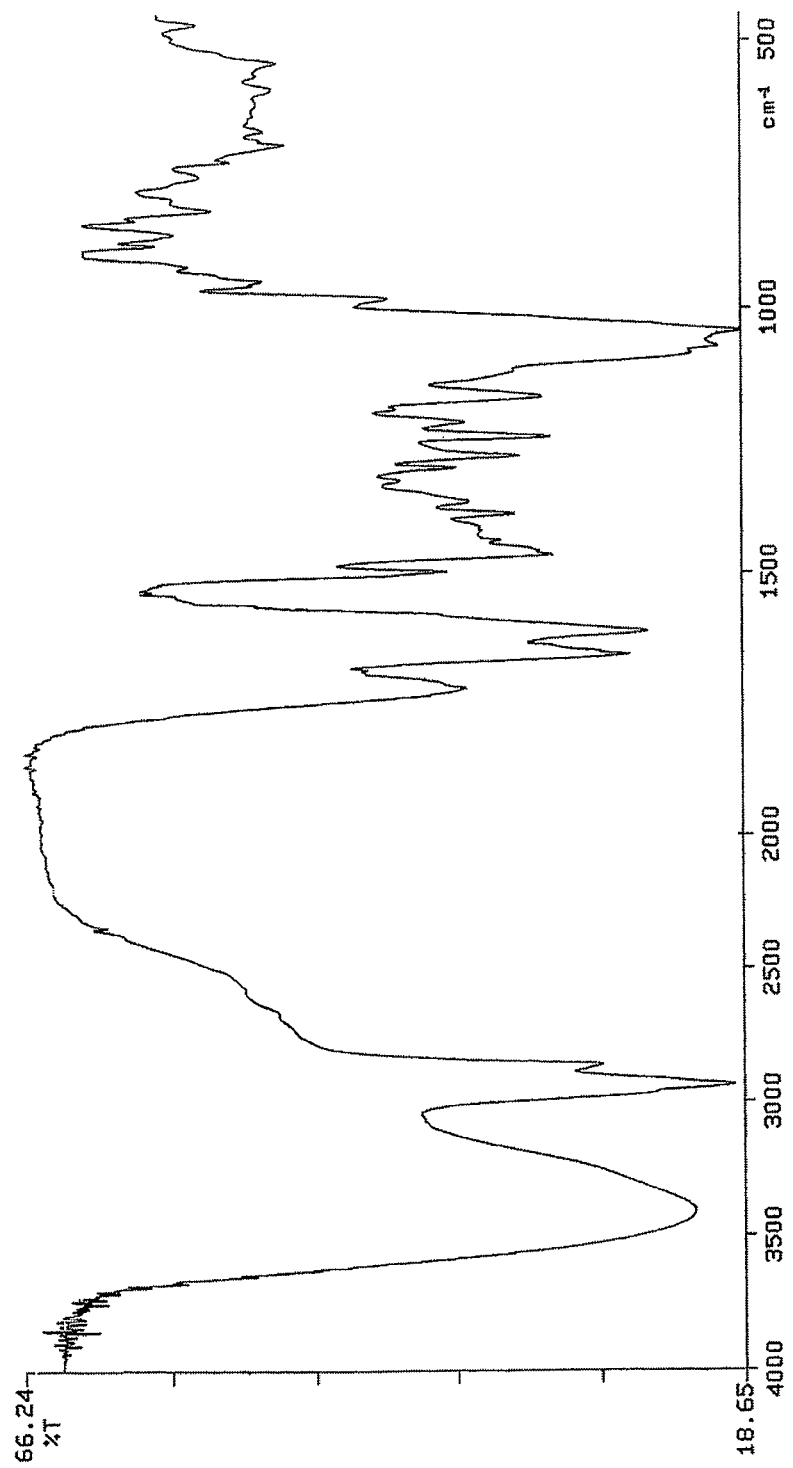
FIG. 4 is an infrared spectrum of dextromethorphan glycyrrhizinate.

The resultant infrared spectrum of dextromethorphan glycyrrhizinate is substantially in accordance with FIG. 4. And FIG. 2 and FIG. 3 is the infrared spectrum of dextromethorphan and glycyrrhizinic acid, respectively.

The result shows that the dextromethorphan glycyrrhizinate has the characteristic of IR(KBr) $v_{max}$: 3400, 2934, 1719, 1655, 1611, 1043 $cm^{-1}$, whereas the dextromethorphan has IR(KBr) $v_{max}$: 2922, 1607, 1506, 1234, 1040, 848, 819 $cm^{-1}$, and the glycyrrhizinic acid has IR(KBr) $v_{max}$: 3435, 2948, 1734, 1648, 1056 $cm^{-1}$.

Figure 5:
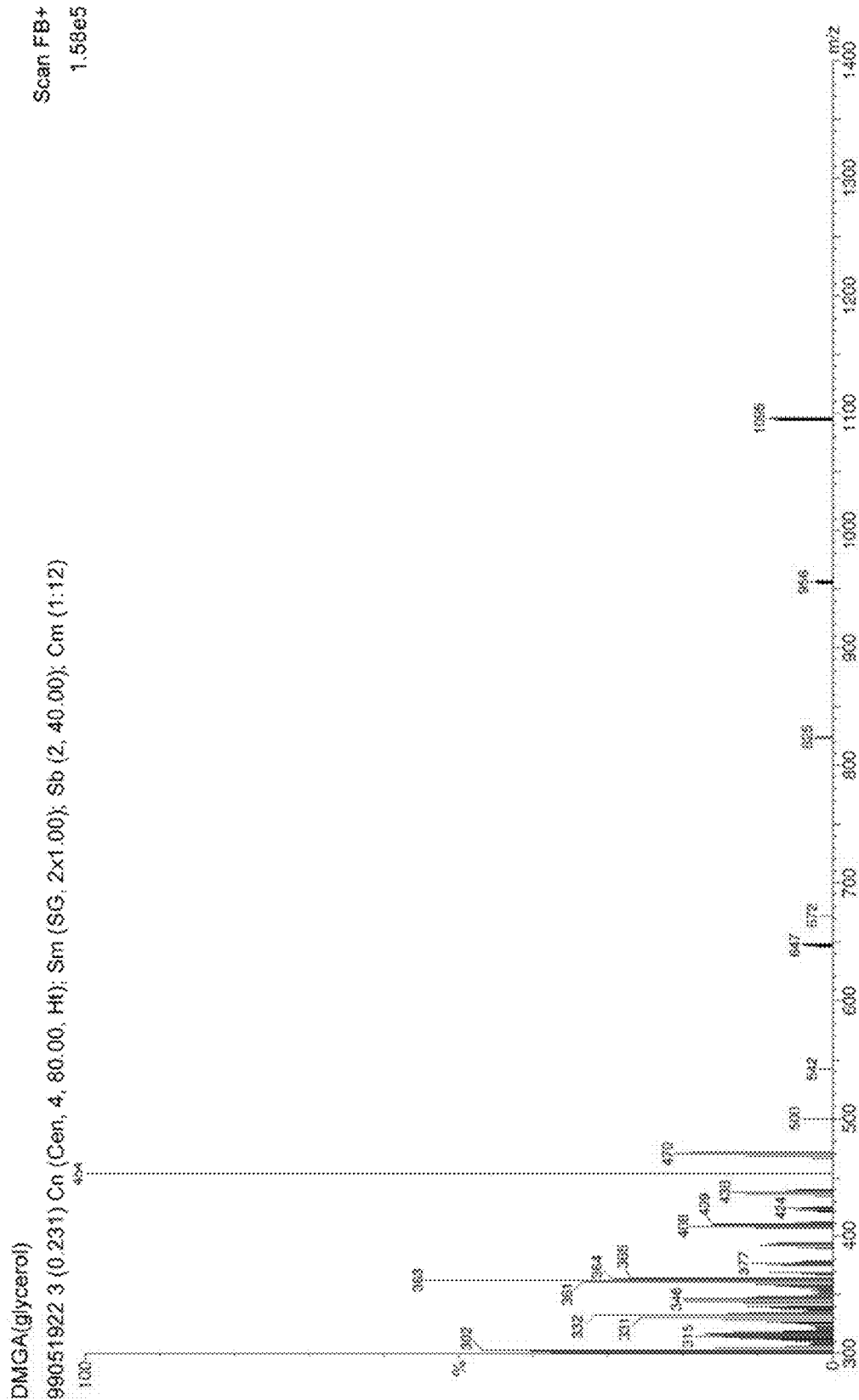
FIG. 5 is a mass spectrum of dextromethorphan glycyrrhizinate.

The resultant mass spectrum of dextromethorphan glycyrrhizinate is substantially in accordance with FIG. 5. The result demonstrates that the molecular weight of the dextromethorphan glycyrrhizinate compound provided by the Example 1 is 1094. And the dextromethorphan glycyrrhizinate compound provided by the Example 1 comprises the characteristic of ESI-MS: m/z 1095 [M+H]$^+$, 454 (100).

Figure 6:
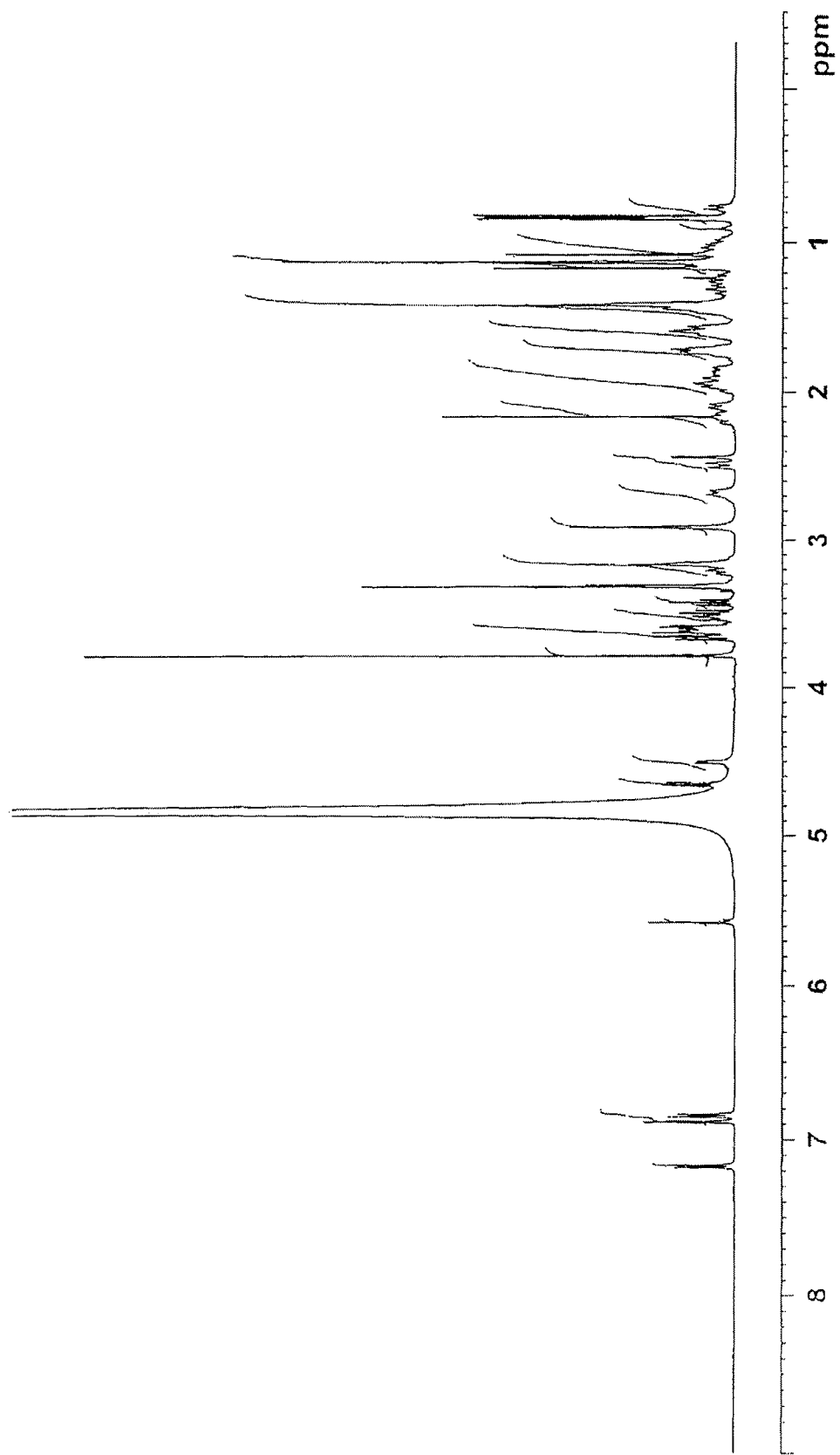
FIG. 6 is a $^1$H-NMR spectrum of dextromethorphan glycyrrhizinate.

The resultant $^1$H-NMR spectrum of dextromethorphan glycyrrhizinate is substantially in accordance with FIG. 6. The result shows that the dextromethorphan glycyrrhizinate compound provided by the Example 1 comprises the following characteristic:

$^1$H NMR(CD$_3$OD, 500 MHz): δ 7.17 (d, J=8.50 Hz, 1H), 6.88 (d, J=2.50 Hz, 1H), 6.85 (dd, J=2.72, 8.50 Hz, 1H), 5.57 (s, 1H), 4.66 (d, J=8.00 Hz, 1H), 4.51 (d, J=7.00 Hz, 1H), 3.78 (s, 3H), 3.60-3.53 (m, 3H), 3.45-3.39 (m, 3H), 3.33-3.26 (m, 1H), 3.23-3.20 (m, 4H), 3.10-3.08 (m, 1H), 2.91 (s, 3H), 2.43 (m, 1H), 2.16-1.94 (m, 3H), 1.87-1.74 (m, 7H), 1.66-1.59 (m, 5H), 1.50-1.47 (m, 6H), 1.36-1.32 (m, 9H), 1.33 (m, 3H), 1.08-0.96 (m, 6H), 1.08 (s, 3H), 1.07 (s, 6H), 0.99 (s, 3H), 0.84 (s, 3H), 0.83 (s, 3H);

Example 2

Preparation of Dimemorfan Glycyrrhizinate Compound by Dimemorfan Free Base and Glycyrrhizinic Acid Dimemorfan free base (0.500 g, 1.96 mmol) and glycyrrhizinic acid (1.610 g, 1.96 mmol) were thoroughly mixed and then added to 24 ml isopropyl alcohol. The resultant mixture was then heated at reflux to provide a clear solution. The resulting clear solution was cooled at 25~30° C., and stirred for 1 hour. The precipitated solid was filtered and washed with 20 ml acetone and dried to produce 1.3 g of dimemorfan glycyrrhizinate.

FT-IR, MS and NMR analyses of dimemorfan glycyrrhizinate are carried out for determining the physical and chemical characteristics of the resultant dimemorfan glycyrrhizinate. And dimemorfan and glycyrrhizinic acid are also tested at the same time for a blank control.

Figure 7:
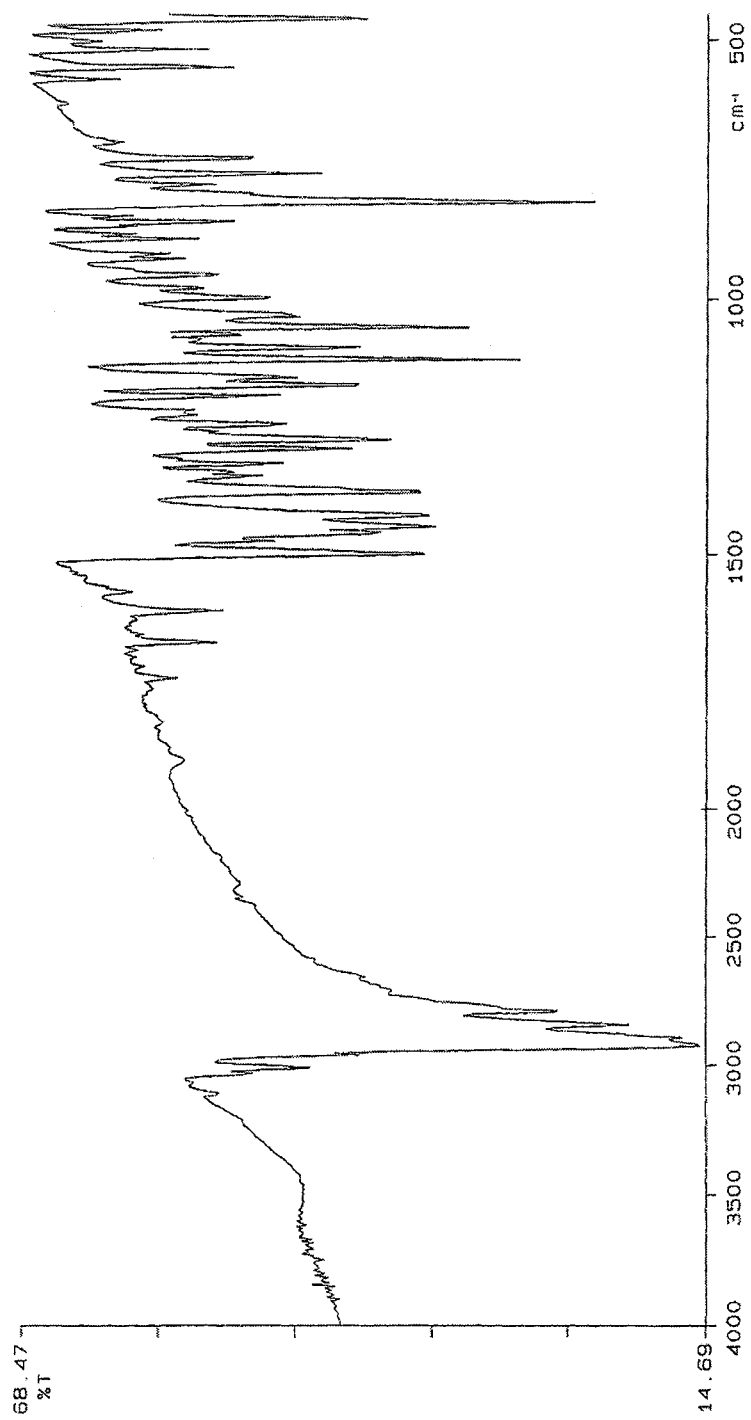
FIG. 7 is an infrared spectrum of dimemorfan.
Figure 8:
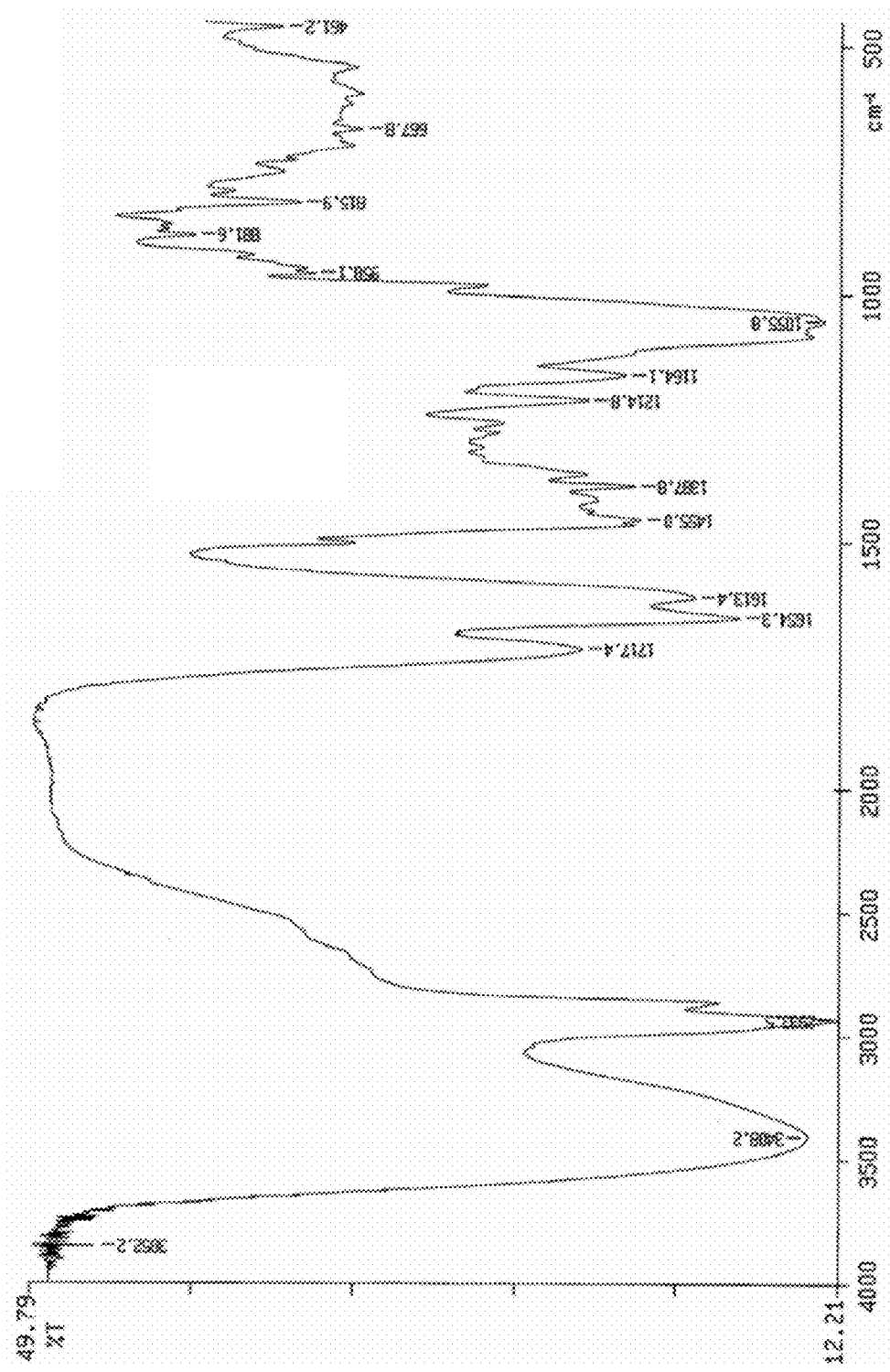
FIG. 8 is an infrared spectrum of dimemorfan glycyrrhizinate.

The resultant infrared spectrum of dimemorfan glycyrrhizinate is substantially in accordance with FIG. 8. And FIG. 7 and FIG. 3 is the infrared spectrum of dimemorfan and glycyrrhizinic acid, respectively.

The result shows that the dimemorfan glycyrrhizinate has the characteristic of IR(KBr) $v_{max}$: 3408, 2934, 1717, 1654, 1613, 1056 cm$^{-1}$, whereas the dimemorfan has IR(KBr) $v_{max}$: 2927, 1501, 1425, 1380, 1120, 814 cm$^{-1}$, and the glycyrrhizinic acid has IR(KBr) $v_{max}$: 3435, 2948, 1734, 1648, 1056 cm$^{-1}$.

Figure 9:
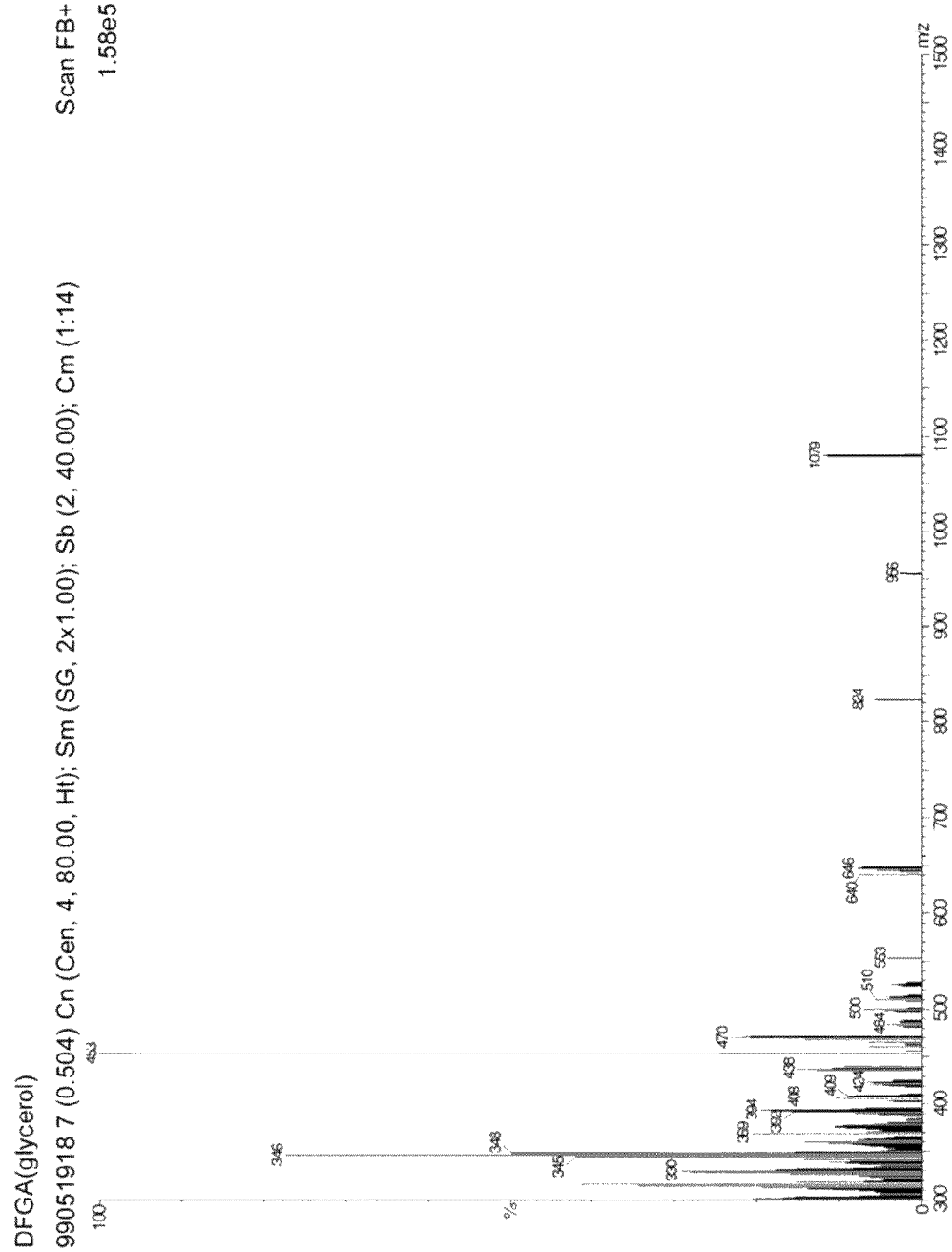
FIG. 9 is a mass spectrum of dimemorfan glycyrrhizinate.

The resultant mass spectrum of dimemorfan glycyrrhizinate is substantially in accordance with FIG. 9. The result demonstrates that the molecular weight of the dextromethorphan glycyrrhizinate compound provided by the Example 2 is 1078. And the dextromethorphan glycyrrhizinate compound provided by the Example 2 comprises the characteristic of ESI-MS: m/z 1079 [M+H]$^+$, 453 (100).

Figure 10:
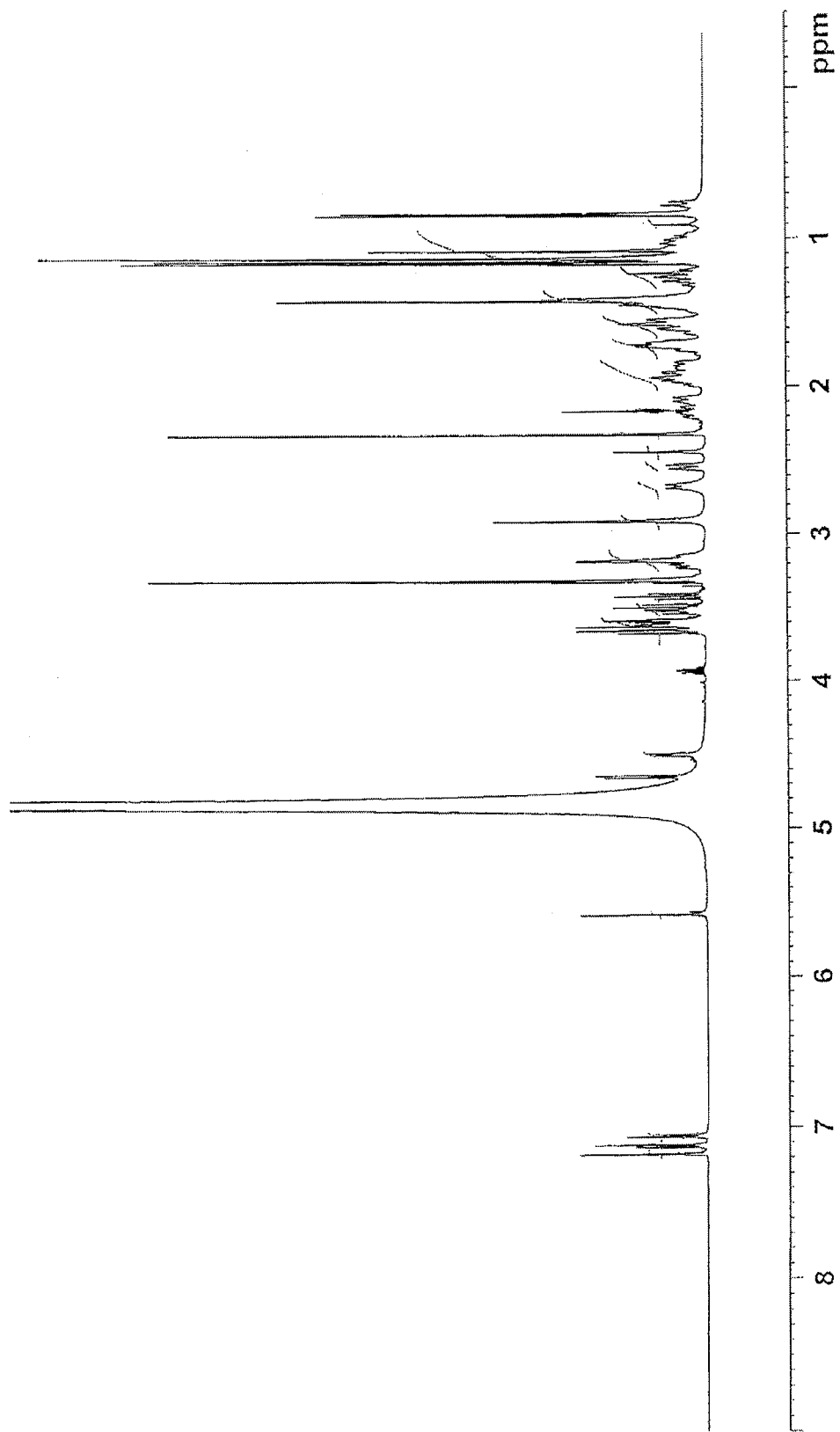
FIG. 10 is a $^1$H-NMR spectrum of dimemorfan glycyrrhizinate.

The resultant $^1$H-NMR spectrum of dimemorfan glycyrrhizinate is substantially in accordance with FIG. 10. The result shows that the dimemorfan glycyrrhizinate compound provided by the Example 2 comprises the following characteristic:

$^1$H NMR(CD$_3$OD, 500 MHz): δ 7.17 (s, 1H), 7.13 (d, J=8.00 Hz, 1H), 7.05 (d, J=8.00 Hz, 1H), 5.57 (s, 1H), 4.64 (d, J=7.50 Hz, 1H), 4.49 (d, J=7.50 Hz, 1H), 3.67-3.58 (m, 5H), 3.52-3.40 (m, 2H), 3.32-3.29 (m, 1H), 3.31-3.30 (m, 4H), 3.29-3.17 (m, 4H), 2.91 (s, 3H), 2.43-2.32 (m, 2H), 2.48-2.44 (m, 1H), 2.32 (s, 1H), 2.16 (s, 3H), 2.09-2.02 (m, 3H), 1.88-1.79 (m, 6H), 1.66-1.61 (m, 4H), 1.52-1.45 (m, 4H), 1.38-0.95 (m, 14H), 1.17 (s, 3H), 1.13 (s, 3H), 1.11 (s, 6H), 1.08 (s, 3H), 0.82 (s, 3H), 0.84 (s, 3H)

Example 3

Evaluation of e-NOS Expression of Dextromethorphan Glycyrrhizinate and Dimemorfan Glycyrrhizinate The e-NOS expression of dextromethorphan glycyrrhizinate and dimemorfan glycyrrhizinate are carried out via the following procedures.

Wistar rat pulmonary artery were incubated in medium with dextromethorphan glycyrrhizinate and dimemorfan glycyrrhizinate in a final concentration of 0.01 mg/ml (10$^{-5}$M) and 0.01 mg/ml (10$^{-5}$ M), respectively. The blank control group were not added with dextromethorphan glycyrrhizinate or dimemorfan glycyrrhizinate. After incubated for 2 hours, the pulmonary artery were lysed in ice-cold homogenization buffer. The homogenates were centrifuged at 13,000 rpm for 10 minutes at 4° C. The protein concentration was determined by the method of Bradford. Samples were denatured and subjected to sodium dodecylsulfate polyacrylamide gel electrophoresis (SDS-PAGE) using a 7.5% running gel. Protein were transferred to polyvinylidene difluoride (PVDF) membrane, and the PVDF membrane was incubated successively at room temperature with 5% nonfat milk-0.1% Tween-Tris buffered saline for 1 hour, with rabbit antibodies specific for anti-eNOS for 1 hour, and with horseradish peroxidase conjugated anti-rabbit IgG antibodies (HRP-conjugated anti-rabbit IgG Ab) for 1 hour. After each incubation, the membrane was washed extensively with 0.1% Tween-Tris buffered saline. The immunoreactive bands were detected by ECL reagents.

The e-NOS expressions of dextromethorphan glycyrrhizinate and dimemorfan glycyrrhizinate are shown in the upper panel of FIG. 1. The expressions of actins are also tested at the same time to be the internal control and are depicted in the middle panel of FIG. 1. The results in the upper panel and the bottom panel show that both dextromethorphan glycyrrhizinate and dimemorfan glycyrrhizinate have good e-NOS expression.

Example 4

Evaluation of Taste of Dextromethorphan Glycyrrhizinate and Dimemorfan Glycyrrhizinate The evaluation the taste of dextromethorphan glycyrrhizinate and dimemorfan glycyrrhizinate are carried out via the following procedures. 5 mg of dextromethorphan hydrobromide or dextromethorphan glycyrrhizinate, 5 mg of dimemorfan phosphate or dimemorfan glycyrrhizinate were tested in the tongue by an expert group. The bitterness was rated using a scale of 0-5 (0 no bitter, 1 just perceptible, 2 slightly bitter, 3 bitter, 4 more bitter, 5 very bitter).

The result of the Example 4 is shown in Table 1 as below.

TABLE 1

Evaluation of taste of dextromethorphan glycyrrhizinate and dimemorfan glycyrrhizinate

| Sample | Average Rating (0-5) |
| --- | --- |
| Dextromethorphan hydrobromide | 3.3 |
| Dextromethorphan glycyrrhizinate | 0.2 |
| Dimemorfan phosphate | 4.1 |
| Dimemorfan glycyrrhizinate | 0.3 |

Example 5

Comparison of solubility of dextromethorphan glycyrrhizinate and dextromethorphan hydrobromide, solubility of dimemorfan glycyrrhizinate and dimemorfan phosphate.

The comparison of solubility of dextromethorphan glycyrrhizinate and dextromethorphan hydrobromide, and the comparison of solubility of dimemorfan glycyrrhizinate and dimemorfan phosphate are carried out by a method of determining the solubility of a chemical compound, wherein step is adding by degrees a volume of water to dissolve 0.1 g of chemical compound until the chemical compound fully dissolves at 28° C.

The result of the Example 5 is shown in Table 2 as below.

TABLE 2

| Comparison of solubility | | |
|---|---|---|
| Solute (chemical compound) | Water quantity for dissolving 0.1 g solute | Solubility (28° C.) |
| Dextromethorphan glycyrrhizinate | 150 ml | 0.067% |
| Dextromethorphan hydrobromide | 4 ml | 2.5% |
| Dimemorfan glycyrrhizinate | 200 ml | 0.05% |
| Dimemorfan phosphate | 4 ml | 2.5% |

Although the particular embodiments of the invention have been described in detail for purpose of illustration, it will be understood by one of ordinary skill in the art that numerous variations will be possible to the disclosed embodiments without going outside the scope of the invention as disclosed in the claims.

What is claimed is:

1. A pharmaceutically acceptable compound, which is a salt of a basic compound of a derivative of morphinan and a carboxyl group-containing agent of formula (I):

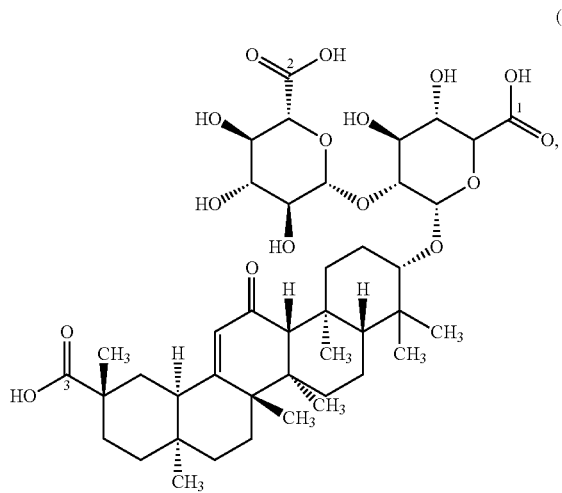

(I)

wherein the derivative of morphinan is selected from the group consisting of dextromethorphan, 3-methoxy-morphinan, dimemorfan, 3-methyl-morphinan, codeine, buprenorphine, butorphanol, nalbuphine, naloxone, nalmefene, naltrexone and oxymorphone.

2. The pharmaceutically acceptable compound of claim 1, which is a 1:1 salt of the basic compound of the derivative of morphinan and glycyrrhizinic acid.

3. The pharmaceutically acceptable compound of claim 1, which is a 2:1 salt of the basic compound of the derivative of morphinan and glycyrrhizinic acid.

4. The pharmaceutically acceptable compound of claim 1, which is a 3:1 salt of the basic compound of the derivative of morphinan and glycyrrhizinic acid.

5. The pharmaceutically acceptable compound of claim 1, exhibiting combined therapeutic effects of the basic group-containing compound of the derivative of morphinan and glycyrrhizinic acid.

6. The pharmaceutically acceptable compound of claim 1, exhibiting combined pharmacology activities selected from the group consisting of an antitussive activity, an analgesic activity, a mucoregulator activity, a cardiovascular protection activity, and a liver protection activity.

7. A method for treating a cough, a pain, a respiratory system disease, or affording protections to cardiovascular and/or liver functions, comprising administering to a subject in need thereof the pharmaceutically acceptable compound of claim 1.

8. A pharmaceutical composition, comprising the pharmaceutically acceptable compound of claim 1 and a pharmaceutically acceptable carrier, diluent or excipient.

9. A pharmaceutical composition, comprising the pharmaceutically acceptable compound of claim 2 and a pharmaceutically acceptable carrier, diluent or excipient.

10. A method for preparation of the pharmaceutically acceptable compound of claim 1, comprising:
    (a) dissolving the basic group-containing compound of the derivative of morphinan in a free base form and the carboxyl group-containing agent in a free acid form in a first solvent to form a solution; and
    (b) removing the first solvent from the solution to obtain the pharmaceutically acceptable coin pound.

11. A method for preparation of the pharmaceutically acceptable compound of claim 1, comprising:
    (a) dissolving the basic group-containing compound of the derivative of morphinan in a free base form and the carboxyl group-containing agent in a free acid form in a first solvent to form a solution; and
    (b) mixing the solution with a second solvent to obtain the pharmaceutically acceptable compound.

* * * * *